(12) United States Patent
Gui et al.

(10) Patent No.: US 11,486,950 B2
(45) Date of Patent: Nov. 1, 2022

(54) SYSTEMS AND METHODS FOR AUTOMATED GRAPHICAL PRESCRIPTION WITH DEEP NEURAL NETWORKS

(71) Applicant: General Electric Company, Schenectady, NY (US)

(72) Inventors: Dawei Gui, Sussex, WI (US); Zachary Slavens, New Berlin, WI (US); Surrendra Markandaya, Waukesha, WI (US); Patrick Quarterman, Brooklyn, NY (US); Hao Shen, Sussex, WI (US)

(73) Assignee: General Electric Company, Schenectady, NY (US)

( * ) Notice: Subject to any disclaimer, the term of this patent is extended or adjusted under 35 U.S.C. 154(b) by 1128 days.

(21) Appl. No.: 16/052,427

(22) Filed: Aug. 1, 2018

(65) Prior Publication Data
US 2020/0041596 A1    Feb. 6, 2020

(51) Int. Cl.
| | |
|---|---|
| G01R 33/54 | (2006.01) |
| A61B 5/00 | (2006.01) |
| A61B 5/055 | (2006.01) |
| G06N 3/04 | (2006.01) |
| G06N 3/08 | (2006.01) |

(52) U.S. Cl.
CPC .......... *G01R 33/543* (2013.01); *A61B 5/0037* (2013.01); *A61B 5/055* (2013.01); *G06N 3/0454* (2013.01); *G06N 3/084* (2013.01)

(58) Field of Classification Search
CPC ........ G06N 3/0454; G06N 3/08; G06N 3/084; G06N 3/04; G06N 20/00; G01R 33/543; G01R 33/54; A61B 5/0037; A61B 5/055; A61B 5/00
See application file for complete search history.

(56) References Cited

U.S. PATENT DOCUMENTS

| | | |
|---|---|---|
| 6,725,077 B1 | 4/2004 | Balloni et al. |
| 7,450,983 B2 | 11/2008 | Weiss |
| 8,045,775 B2 | 10/2011 | Volkau et al. |

(Continued)

FOREIGN PATENT DOCUMENTS

| | | |
|---|---|---|
| CN | 102369259 A | 3/2012 |
| WO | 2008024082 A2 | 2/2008 |

OTHER PUBLICATIONS

Yu, H. et al., "Anatomic Labelling of PET Brain Images with Automatic Detection of AC and PC," Journal of Digital Imaging, vol. 11, No. 3, Suppl. 1, Aug. 1998, 3 pages.

(Continued)

*Primary Examiner* — Tuan H Nguyen
(74) *Attorney, Agent, or Firm* — McCoy Russell LLP (57) ABSTRACT

Methods and systems are provided for automated graphical prescriptions with deep learning systems. In one embodiment, a method for a medical imaging system comprises acquiring, by the medical imaging system, localizer images of a subject, generating, by a trained neural network system, a graphical prescription using the localizer images, and performing, by the medical imaging system, a scan of the subject according to the graphical prescription. In this way, a desired region of interest of the subject may be accurately scanned with minimal input from an operator of the medical imaging system.

20 Claims, 9 Drawing Sheets

(56) References Cited

U.S. PATENT DOCUMENTS

| | | | |
|---|---|---|---|
| 8,363,918 B2* | 1/2013 | Schwing | G06T 7/77 |
| | | | 382/131 |
| 8,565,505 B2* | 10/2013 | Bergmans | G01R 33/54 |
| | | | 600/407 |
| 8,737,712 B2 | 5/2014 | Geiger | |
| 8,811,699 B2 | 8/2014 | Lu et al. | |
| 11,176,484 B1* | 11/2021 | Dorner | G06F 16/738 |
| 2007/0076927 A1 | 4/2007 | Nagaraja Rao et al. | |
| 2007/0127792 A1 | 6/2007 | Virtue | |
| 2011/0206260 A1 | 8/2011 | Bergmans | |

OTHER PUBLICATIONS

Itti, L. et al., "Automatic Scan Prescription for Brain MRI," Magnetic Resonance in Medicine, vol. 45, No. 3, Mar. 2001, 9 pages.

Liu, D. et al., "Vascular Landmark Detection in 3D CT Data," Proceedings vol. 7965 of the 2011 SPIE Medical Imaging: Biomedical Applications in Molecular, Structural, and Functional Imaging, Mar. 15, 2011, Lake Buena Vista (Orlando), Florida, 7 pages.

Prasoon, A. et al., "Deep Feature Learning for Knee Cartilage Segmentation Using a Triplanar Convolutional Neural Network," Proceedings (Part II) of the 16th International Conference on Medical Image Computing and Computer-Assisted Intervention—MICCAI 2013, Sep. 22, 2013, Nagoya, Japan, 8 pages.

Roth, H. et al., "A New 2.5D Representation for Lymph Node Detection using Random Sets of Deep Convolutional Neural Network Observations," Proceedings of the 17th International Conference on Medical Image Computing and Computer-Assisted Intervention—MICCAI 2014, Sep. 14, 2014, Boston, Massachusetts, 11 pages.

Lecun, Y. et al., "Deep Learning," Nature, vol. 521, No. 7553, May 28, 2015, 9 pages.

Zheng, Y. et al., "3D Deep Learning for Efficient and Robust Landmark Detection in Volumetric Data," Proceedings of the 18th International Conference on Medical Image Computing and Computer-Assisted Intervention—MICCAI 2015, Oct. 5, 2015, Munich, Germany, 8 pages.

Wu, H. et al., "Max-Pooling Dropout for Regularization of Convolutional Neural Networks," Cornell University Library Website, Available Online at https://arxiv.org/ftp/arxiv/papers/1512/1512.01400.pdf, Dec. 4, 2015, 8 pages.

Zheng, S. et al., "Conditional Random Fields as Recurrent Neural Networks," Proceedings of the 2015 IEEE International Conference on Computer Vision (ICCV), Dec. 7, 2015, Santiago, Chile, 9 pages.

Le, Q., "A Tutorial on Deep Learning Part 2: Autoencoders, Convolutional Neural Networks and Recurrent Neural Networks," Google Brain, Google Inc., University of Stanford Computer Science Website, Available Online at https://cs.stanford.edu/~quocle/tutorial2.pdf, Oct. 20, 2015, 20 pages.

Le, Q., "A Tutorial on Deep Learning Part 1: Nonlinear Classifiers and the Backpropagation Algorithm," Google Brain, Google Inc., University of Stanford Computer Science Website, Available Online at https://cs.stanford.edu/~quocle/tutorial1.pdf, Dec. 13, 2015, 18 pages.

European patent application 19188483.2 filed Jul. 25, 2019, Search Report dated Dec. 16, 2019, 14 pages.

Xulei Yang et al: "Automatic detection of anatomical landmarks in brain MR scanning using multi-task deep neural networks", Neurocomputing, Apr. 1, 2019 (Apr. 1, 2019), XP055649903, Amsterdam, NL ISSN: 0925-2312, DOI: 10.1016/j.neucom.2018.10.105 1-20.

* cited by examiner

SYSTEMS AND METHODS FOR AUTOMATED GRAPHICAL PRESCRIPTION WITH DEEP NEURAL NETWORKS

FIELD

Embodiments of the subject matter disclosed herein relate to medical imaging, such as magnetic resonance imaging (MRI), and more particularly, to automatically generating graphical prescriptions for medical imaging with deep neural networks.

BACKGROUND

Medical imaging systems are often used to obtain internal physiological information of a subject, such as a patient. For example, a medical imaging system may be used to obtain images of the bone structure, the brain, the heart, the lungs, and various other features of a subject. Medical imaging systems may include magnetic resonance imaging (MRI) systems, computed tomography (CT) systems, x-ray systems, ultrasound systems, and various other imaging modalities.

Prior to performing a diagnostic scan of the subject, a low-resolution or low-dose scan of the subject, often referred to as a scout scan or a localizer scan, may be performed to obtain a scout image or localizer image of the subject's internal anatomy. An operator of the medical imaging system may plan the diagnostic scan of the subject according to the scout image or localizer image, to ensure that the full-strength diagnostic scan of the subject correctly images the subject as desired.

BRIEF DESCRIPTION

In one embodiment, a method for a medical imaging system comprises acquiring, by the medical imaging system, localizer images of a subject, generating, by a trained neural network system, a graphical prescription using the localizer images, and performing, by the medical imaging system, a scan of the subject according to the graphical prescription. In this way, a desired region of interest of the subject may be accurately scanned with minimal input from an operator of the medical imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of automated graphical prescription for imaging systems. In particular, systems and methods are provided for automatically generating a graphical prescription with a deep neural network system for imaging a subject with an imaging system, such as the MRI system depicted in FIG. 1. A deep neural network system, such as the system depicted in FIG. 2, includes a variety of convolutional neural networks such as a feature representation network, an anatomy classification network, a key frame identifier network, and a graphical prescription network. The neural networks, sometimes also referred to herein simply as networks, may leverage the learning of each other network to increase the accuracy of each network as depicted by the neural network architecture in FIGS. 3A, 3B, and 4. A method for using the automatically-generated graphical prescription, such as the method depicted in FIG. 5, includes pre-processing localizer images, extracting features from the localizer images, classifying anatomy in the localizer images, identifying key frames of the localizer images, automatically generating a graphical prescription, and scanning the subject according to the graphical prescription. In addition, the automatically-generated graphical prescription may be used for follow-up scans of the subject, thereby simplifying the workflow and resulting in consistent images across different scanning sessions.

While the methods for automatic graphical prescription are described herein with regard to an MRI system, it should be appreciated that the methods may be implemented with other imaging modalities.

Furthermore, the brain is used as an exemplary anatomy in the discussion of the methods herein below, though it should be appreciated that the systems and methods described herein are applicable to any appropriate anatomies. For example, the deep learning system described herein may be used to generate graphical prescriptions for spines, abdomens, knees, hearts, and other anatomies.

Figure 1:
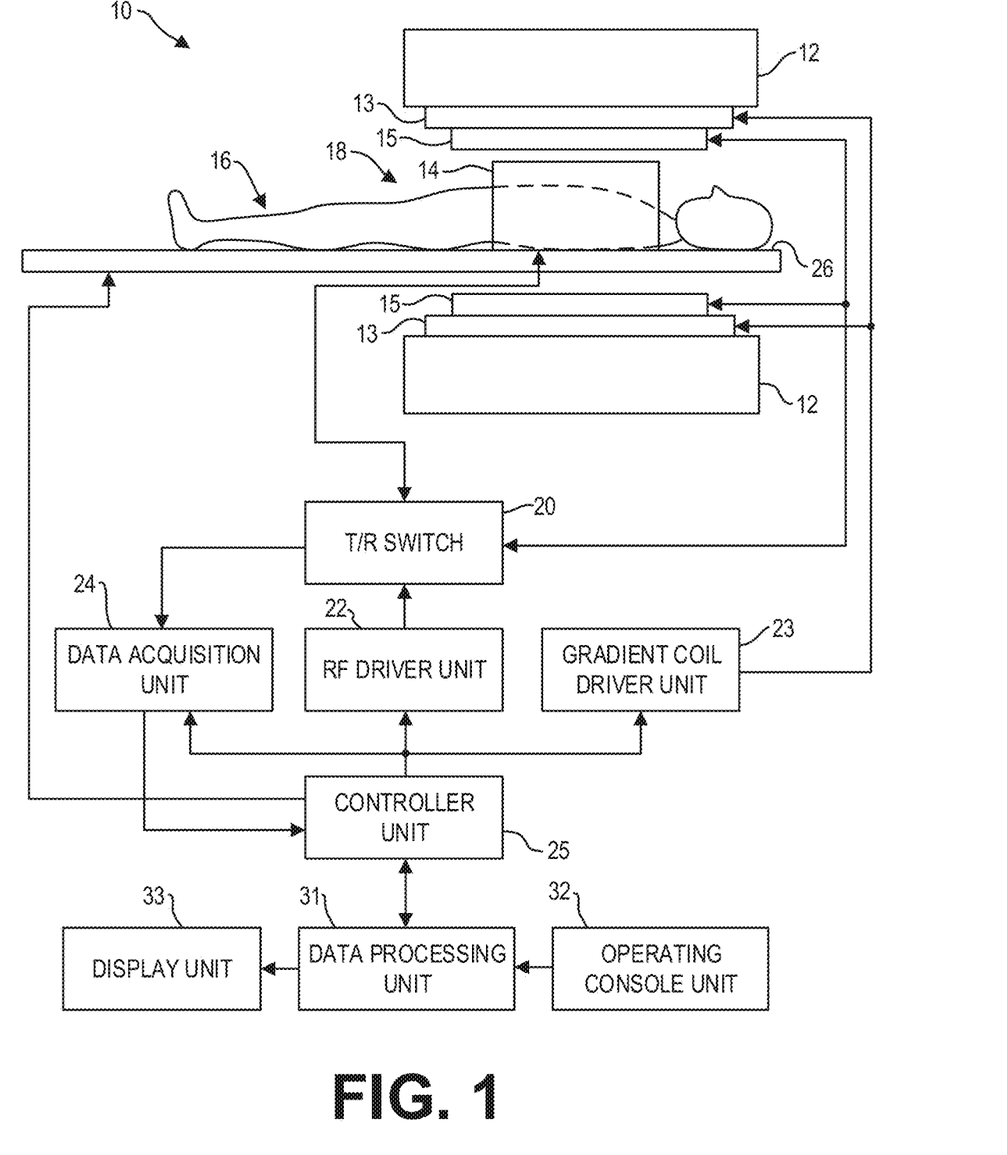
FIG. 1 is a block diagram of an Mill system according to an exemplary embodiment.

FIG. 1 illustrates a magnetic resonance imaging (MRI) apparatus 10 that includes a magnetostatic field magnet unit 12, a gradient coil unit 13, an RF coil unit 14, an RF body coil unit 15, a transmit/receive (T/R) switch 20, an RF driver unit 22, a gradient coil driver unit 23, a data acquisition unit 24, a controller unit 25, a patient bed 26, a data processing unit 31, an operating console unit 32, and a display unit 33. The MRI apparatus 10 transmits electromagnetic pulse signals to a subject 16 placed in an imaging space 18 with a magnetostatic field formed to perform a scan for obtaining magnetic resonance (MR) signals from the subject 16 to reconstruct an image of a slice of the subject 16 based on the MR signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field $B_0$.

The MRI apparatus 10 also includes the gradient coil unit 13 that generates a gradient magnetic field in the imaging space 18 so as to provide the MR signals received by the RF coil unit 14 with three-dimensional positional information. The gradient coil unit 13 includes three gradient coil systems, each of which generates a gradient magnetic field which inclines into one of three spatial axes perpendicular to each other, and generates a gradient field in each of frequency-encoding direction, phase-encoding direction, and slice-selection direction in accordance with the imaging condition. More specifically, the gradient coil unit 13 applies a gradient field in the slice-selection direction of the subject 16, to select the slice; and the RF coil unit 14 transmits an RF pulse to a selected slice of the subject 16 and excites it. The gradient coil unit 13 also applies a gradient field in the phase-encoding direction of the subject 16 to phase encode the MR signals from the slice excited by the RF pulse. The gradient coil unit 13 then applies a gradient field in the frequency-encoding direction of the subject 16 to frequency encode the MR signals from the slice excited by the RF pulse.

The RF coil unit 14 is disposed, for example, to enclose the region to be imaged of the subject 16. In the static magnetic field space or imaging space 18 where a static magnetic field $B_0$ is formed by the magnetostatic field magnet unit 12, the RF coil unit 14 transmits, based on a control signal from the controller unit 25, an RF pulse that is an electromagnetic wave to the subject 16 and thereby generates a high-frequency magnetic field $B_1$. This excites a spin of protons in the slice to be imaged of the subject 16. The RF coil unit 14 receives, as an MR signal, the electromagnetic wave generated when the proton spin thus excited in the slice to be imaged of the subject 16 returns into alignment with the initial magnetization vector. The RF coil unit 14 may transmit and receive an RF pulse using the same RF coil.

The RF body coil unit 15 is disposed, for example, to enclose the imaging space 18, and produces RF magnetic field pulses $B_1$ orthogonal to the main magnetic field $B_0$ produced by the magnetostatic field magnet unit 12 within the imaging space 18 to excite the nuclei. In contrast to the RF coil unit 14, which may be easily disconnected from the MR apparatus 10 and replaced with another RF coil unit, the RF body coil unit 15 is fixedly attached and connected to the MRI apparatus 10. Furthermore, whereas local coils such as those comprising the RF coil unit 14 can transmit to or receive signals from only a localized region of the subject 16, the RF body coil unit 15 generally has a larger coverage area and can be used to transmit or receive signals to the whole body of the subject 16. Using receive-only local coils and transmit body coils provides a uniform RF excitation and good image uniformity at the expense of high RF power deposited in the subject 16. For a transmit-receive local coil, the local coil provides the RF excitation to the region of interest and receives the MR signal, thereby decreasing the RF power deposited in the subject 16. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in a receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 14 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a preamplifier (not shown), a phase detector (not shown), and an analog/digital converter (not shown) used to acquire the MR signals received by the RF coil unit 14. In the data acquisition unit 24, the phase detector phase detects, using the output from the RF oscillator of the RF driver unit 22 as a reference signal, the MR signals received from the RF coil unit 14 and amplified by the preamplifier, and outputs the phase-detected analog MR signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded, in some embodiments. The program when executed by the computer causes various parts of the apparatus to carry out operations corresponding to predetermined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform pre-determined data processing is recorded. The data processing unit 31 is connected to the controller unit 25 and performs data processing based on control signals received from the controller unit 25. The data processing unit 31 is also connected to the data acquisition unit 24 and generates spectrum data by applying various imaging processing operations to the MR signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a slice image of the subject 16 generated by the data processing unit 31.

Figure 2:
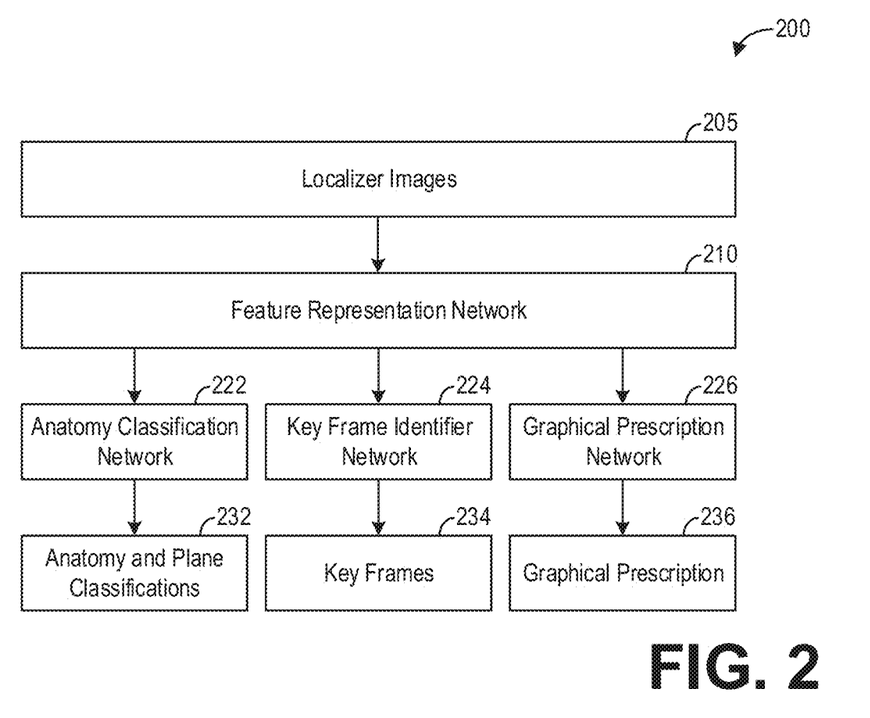
FIG. 2 shows a high-level block diagram illustrating a deep learning architecture for automated graphical prescription according to an exemplary embodiment.

The MRI apparatus 10 may be configured with a deep learning system for automatically generating graphical prescriptions. As an illustrative example, FIG. 2 shows a high-level block diagram illustrating a deep learning architecture 200 for automated graphical prescription according to an embodiment. The deep learning architecture 200 is described with regard to the systems and components of FIG. 1, though it should be understood that the deep learning architecture 200 may be implemented with other systems and components without departing from the scope of the present disclosure. For example, the deep learning architecture 200 may be implemented in a non-transitory memory and may be executable by one or more processors of the MRI apparatus 10, such as the data processing unit 31. In some embodiments, the deep learning architecture 200 may be implemented on an edge device connected to the MRI apparatus 10. In some embodiments, the deep learning architecture 200 may be implemented in a cloud in communication with the MRI apparatus 10. In some embodiments, portions of the deep learning architecture are implemented on different devices, such as any appropriate combination of the MRI apparatus 10, the edge device, the cloud, etc.

Referring to FIG. 2, the localizer images 205 may be acquired as two-dimensional localizers or a three-dimensional localizer volume. In some embodiments, the MRI apparatus 10 is controlled to acquire a set of three-plane, low-resolution, large field-of-view two-dimensional localizer images 205. In some embodiments, the MRI apparatus 10 is controlled to acquire a three-dimensional localizer image volume. The three-dimensional localizer image volume may form the localizer images 205 or be re-formatted or projected into multi-plane two-dimensional space to form the localizer images 205. The localizer images 205 may comprise, for example, a standard SSFSE/GRE localizer, a three-dimensional low-resolution volume, or other two-dimensional localizers with T2/T1/PD contrasts depending on anatomy or clinical needs. Further, a sagittal T2 FSE scan may be used to identify the multi-plane multi-angle axial localizer scan.

In some embodiments, the localizer images 205 may be further pre-processed. For example, since original localizer images may come from different systems with different shading patterns, and with different pulse sequences resulting in different contrasts, a dedicated pre-processing is performed for deep learning architectures to extract the intrinsic features from the acquired localizer images. Pre-processing the localizer images 205 may therefore include performing contrast normalization on the localizer images 205. Global contrast normalization prevents images from having varying amounts of contrast by subtracting the mean from each image, then rescaling it so that the standard deviation across its pixels is equal to some constant. Since global contrast normalization sometimes fails to highlight image features desired to stand out, such as edges and corners, both global contrast normalization and local contrast normalization may be used. Pre-processing may further include data resampling. For example, since both multi-slice two-dimensional and three-dimensional localizers contain a volume data, resampling in different orientations provides additional inputs as the training datasets for the neural network architecture to increase the training size, thereby improving the training results.

As depicted, the deep learning architecture 200 includes a feature representation network 210, an anatomy classification network 222, a key frame identifier network 224, and a graphical prescription network 226. As discussed below, the networks 210, 222, 224, and 226 may share layers to leverage the learned weights for different tasks.

The localizer images 205 are input to a feature representation network 210, which is configured to extract features from the localizer images 205. The feature representation network 210 may comprise a convolutional neural network including a plurality of convolutional layers or any other appropriate type of neural network.

The output of the feature representation network 210 is input to the anatomy classification network 222, which in turn outputs anatomy and plane classifications 232. To that end, the anatomy classification network 222 may comprise a feedforward fully-connected neural network including a plurality of fully-connected layers. It should be appreciated that the anatomy classification network 222 may comprise any appropriate type of classification algorithm, including but not limited to a support vector machine (SVM). The anatomy and plane classifications 232 output by the anatomy classification network 222 comprise a classification of the anatomy and planes of the localizer images 205. For example, if a localizer image of the localizer images 205 comprises a sagittal view of a brain, the anatomy and plane classification 232 output by the anatomy classification network 222 for the localizer image comprises a classification of brain and sagittal.

Furthermore, it should be appreciated that the feature representation network 210 may be at least initially trained in combination with the anatomy classification network 222. For example, a training dataset comprising a large plurality of localizer images 205 of different anatomies in different planes, along with labels for each of the plurality of localizer images 205 indicating the anatomies and planes, may be input to the feature representation network 210 and the anatomy classification network 222 to train the networks, which may be considered in such an example to be a single network comprising a plurality of convolutional layers followed by a plurality of fully-connected layers. The networks may thus be trained in this way using backpropagation, as known in the art, to adjust and learn the weights such that the anatomy classification network 222 accurately classifies the anatomy and plane of a localizer image 205 input to the feature representation network 210.

The outputs of at least a subset of layers of the feature representation network 210 are input to the key frame identifier network 224, which in turn outputs key frames 234 of the localizer images 205. That is, rather than inputting only the output of the final convolutional layer of the feature representation network 210 into the key frame identifier network 224, the output of multiple convolutional layers of the feature representation network 210 may be directly output from the feature representation network 210 and input to the key frame identifier network. Key frames may comprise images or frames of the localizer images 205 that include one or more anatomical landmarks that correspond to or indicate a standard reference plane for imaging the anatomy. As an illustrative and non-limiting example, if the localizer images 205 depict a brain of a subject, the identified key frames 234 may include the images of the localizer images 205 that include the anterior commissure-posterior commissure (AC-PC) line, which comprises the line that connects two distinct anatomic structures of the brain, namely the anterior commissure (AC) and the posterior commissure (PC) of the brain. The identified key frames may additionally or alternatively include frames or images of the localizer images 205 that include the orbitomeatal (OM) line, which passes through the outer canthus of the eye and the center of the external auditory meatus. The AC-PC line and the OM line are often used to define the standard axial imaging plane, for example. To that end, the key frame identifier network 224 may be trained with a training dataset including a large plurality of localizer images, wherein each of the plurality of localizer images is labeled as either a key frame or a non-key frame. Additionally, in some examples the specific anatomical landmarks of the localizer images of the training dataset may be labeled in the training dataset. The key frame identifier network 224 may thus be trained using backpropagation with the training dataset by inputting the training dataset into the feature representation network 210 and the key frame identifier network 224.

Similar to the key frame identifier network 224, the outputs of at least a subset of the convolutional layers of the feature representation network 210 are input to the graphical prescription network 226, which in turn outputs a graphical prescription 236. The graphical prescription 236 may comprise graphical prescription marks such as points, lines, boxes, or other shapes overlaid on key frames 234 of the localizer images 205 to indicate a desired region of interest, as well as indicate the field of view, spacing, thickness, location, and orientation of the desired region of interest. In this way, the graphical prescription 236 automatically prescribes both volume orientation and volume coverage to ensure that the desired region of interest is accurately imaged during the full diagnostic scan.

Figure 3A:
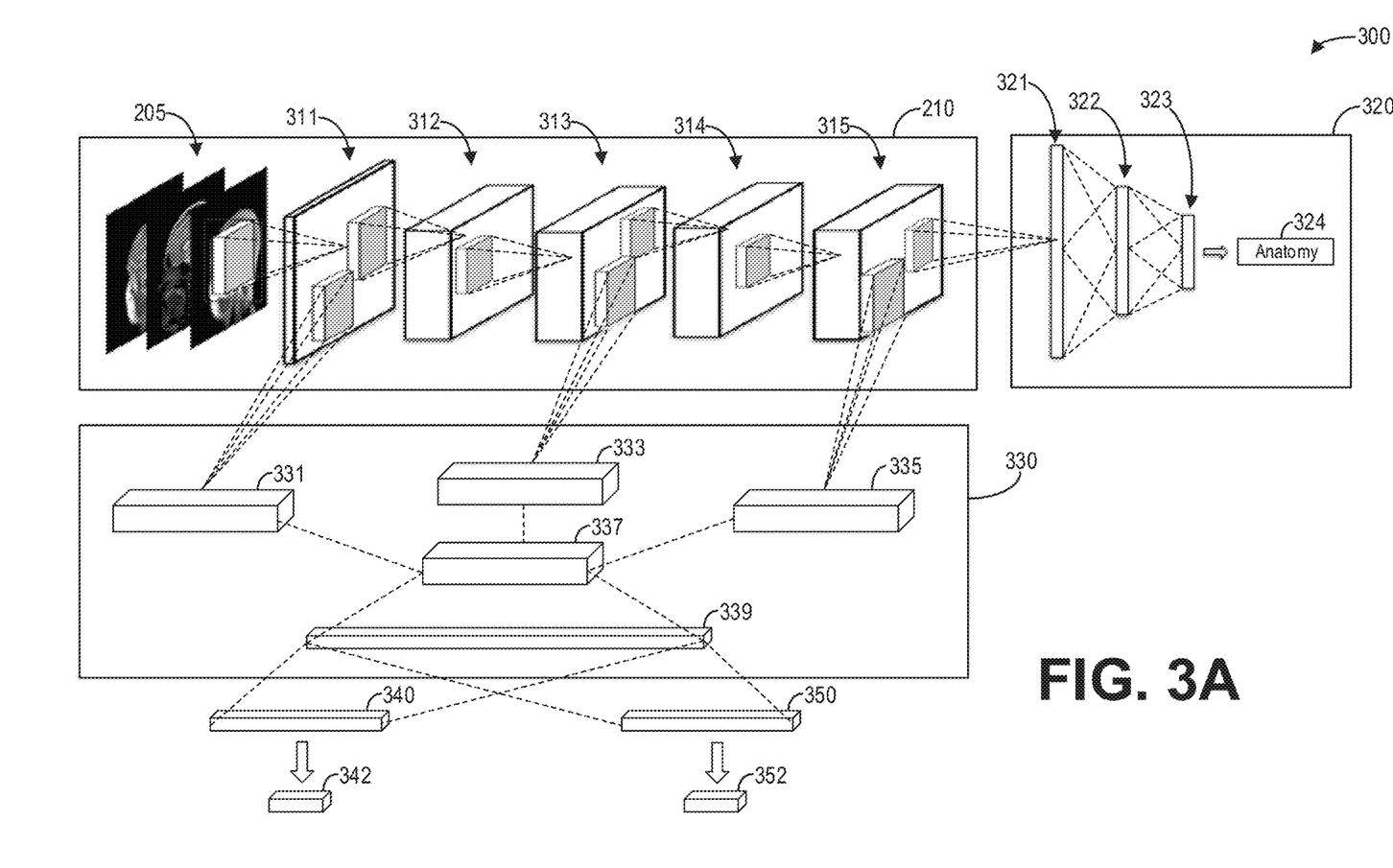
FIG. 3A shows a schematic diagram illustrating example layers of a deep learning architecture for classifying anatomies, identifying key frames, and generating graphical prescriptions according to an exemplary embodiment.

FIG. 3A shows a schematic diagram illustrating example layers of a deep learning architecture 300 for classifying anatomies, identifying key frames, and generating graphical prescriptions according to an exemplary embodiment. In particular, the deep learning architecture 300 depicts a more detailed view of an example configuration of certain components of the deep learning architecture 200 described hereinabove with regard to FIG. 2, including the feature representation network 210, the anatomy classification network 222, the key frame identifier network 224, and the graphical prescription network 226.

As depicted, the feature representation network 210 includes a first convolutional layer 311, a second convolutional layer 312, a third convolutional layer 313, a fourth convolutional layer 314, and a fifth convolutional layer 315. The first convolutional layer 311 receives the localizer images 205 (e.g., acquired localizer images or processed localizer images) as input and outputs the convolved results to the second convolutional layer 312. The second convolutional layer 312 convolves the convolved results from the first convolutional layer 311 and outputs the convolved results to the third convolutional layer 313. The third convolutional layer 313 convolves the convolved results received from the second convolutional layer and outputs the convolved results to the fourth convolutional layer 314. The fourth convolutional layer 314 convolves the convolved results received from the third convolutional layer 313 and outputs the convolved results to the fifth convolutional layer 315. The fifth convolutional layer 315 convolves the convolved results received from the fourth convolutional layer 314 and outputs the convolved results to the anatomy classification network 320.

It should be appreciated that, although not depicted, the feature representation network 210 may include one or more pooling layers between one or more of the convolutional layers 311, 312, 313, 314, and 315 for pooling or subsampling the output of the convolutional layers, thereby reducing the dimensionality between convolutional layers. For example, a max pooling layer (not shown) may be positioned between the first convolutional layer 311 and the second convolutional layer 312. It should also be appreciated that any appropriate type of neural network and any appropriate number of layers may be used for the feature representation network 210.

Still referring to FIG. 3A, the anatomy classification network 320 comprises a feedforward fully-connected neural network, which includes a first layer 321, a second layer 322, a third layer 323, and an output layer 324. The first layer 321, the second layer 322, and the third layer 323 may comprise fully-connected layers rather than convolutional layers, while the output layer 324 outputs the anatomy and plane classifications 232 described hereinabove. It should be appreciated that any appropriate type of neural network and any appropriate number of layers may be used for the anatomy classification network 320.

Furthermore, as depicted, the outputs of at least a subset of the layers of the feature representation network 210 (e.g., the first convolutional layer 311, the third convolution layer 313, and the fifth convolution layer 315) are directed to a hyper network 330 for key frame identification and graphical prescription generation. For example, as depicted, the output of the first convolution layer 311 of the feature representation network 210 is input to a first convolutional layer 331 of the hyper network 330, the output of the third convolutional layer 313 of the feature representation network 210 is input to a second convolution layer 333 of the hyper network 330, and the output of the fifth convolutional layer 315 of the feature representation network 210 is input to a third convolution layer 335 of the hyper network 330. In this way, different levels of abstractions of the feature representations generated by the feature representation network 210 are used as inputs to the hyper network 330. In some embodiments, the outputs of all layers of the feature representation network 210 are directed to the hyper network 330.

The output of the first convolutional layer 331, the second convolutional layer 333, and the third convolutional layer 335 of the hyper network 330 are input to a shared convolutional layer 337, thereby fusing the convolutions of the convolutional layers 331, 333, and 335. The convolved output of the shared convolutional layer 337 is then input to a fully-connected layer 339.

The output of the fully-connected layer 339 is provided to a fully-connected layer 340 for key frame identification and a fully-connected layer 350 for graphical prescription generation. The output 342 of the fully-connected layer 340 thus comprises an identification of key frames while the output 352 of the fully-connected layer 350 comprises a graphical prescription.

The fully-connected layer 340 in combination with the hyper network 330 constitutes a hyper key frame classification neural network. Similarly, the fully-connected layer 350 in combination with the hyper network 330 constitutes a hyper graphical prescription generation neural network. As depicted, the hyper key frame identification neural network and the hyper graphical prescription generation neural network share a plurality of layers, specifically the depicted layers forming the hyper network 330. In this way, the training of each hyper network is leveraged to improve the accuracy of the other network.

Figure 3B:
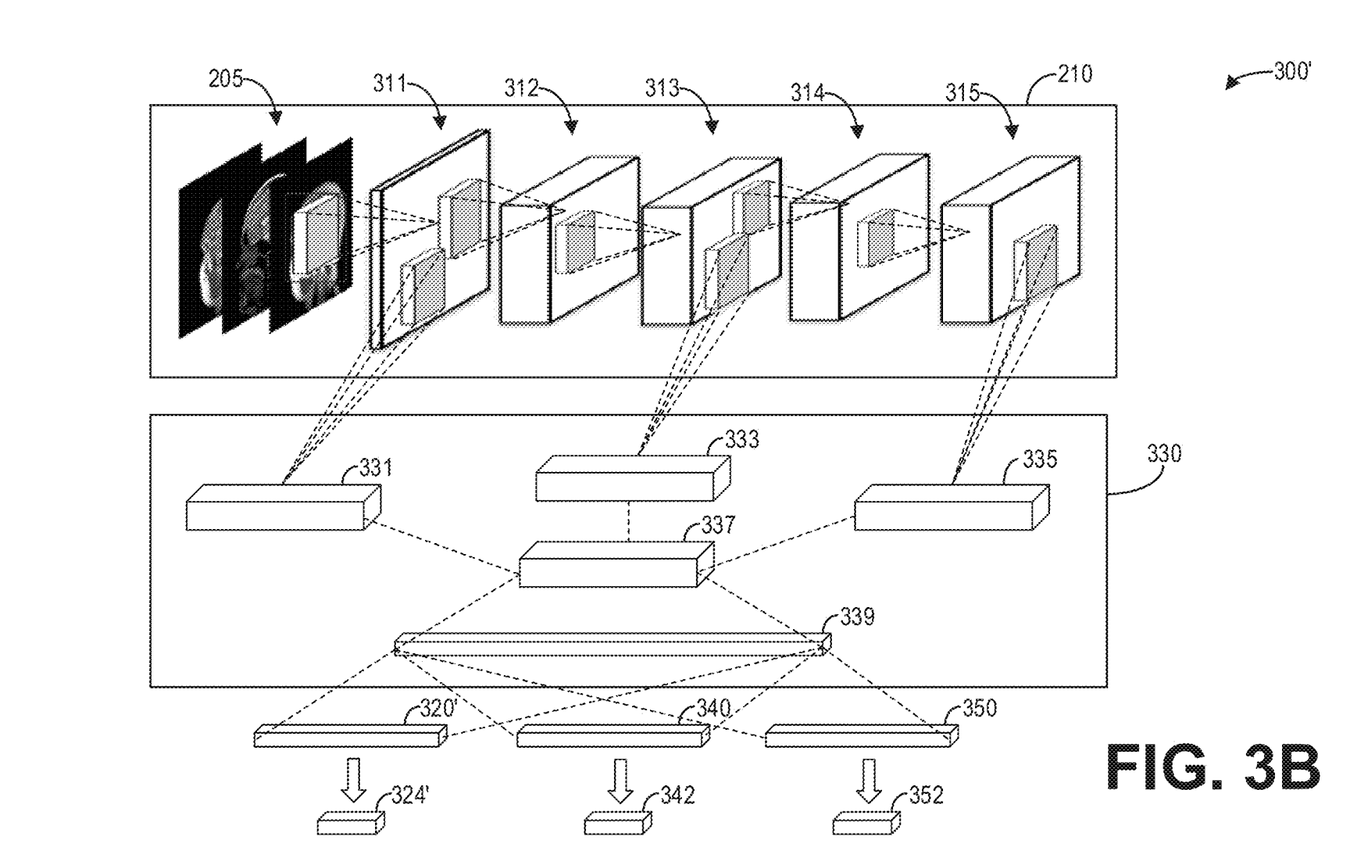
FIG. 3B shows a schematic diagram illustrating example layers of a deep learning architecture for classifying anatomies, identifying key frames, and generating graphical prescriptions according to another exemplary embodiment.

FIG. 3B shows a schematic diagram illustrating example layers of a deep learning architecture 300' for classifying anatomies, identifying key frames, and generating graphical prescriptions according to another exemplary embodiment. Components of the deep learning architecture 300' are the same as or similar to corresponding components of the deep learning architecture 300 of FIG. 3A except that the anatomy classification network 320 of FIG. 3A is replaced by a fully-connected layer 320' in FIG. 3B for anatomy and plane classifications. The fully-connected layer 320', like the fully-connected layers 340 and 350, receives the output of the fully-connected layer 339. The fully-connected layer 320' in combination with the hyper network 330 comprises constitutes a hyper anatomy classification neural network. The output 324' of the fully-connected layer 320' thus comprises an anatomy and plane classification.

It should be appreciated that any appropriate type of neural network and any appropriate number of layers may be used for the hyper network 330.

Figure 4:
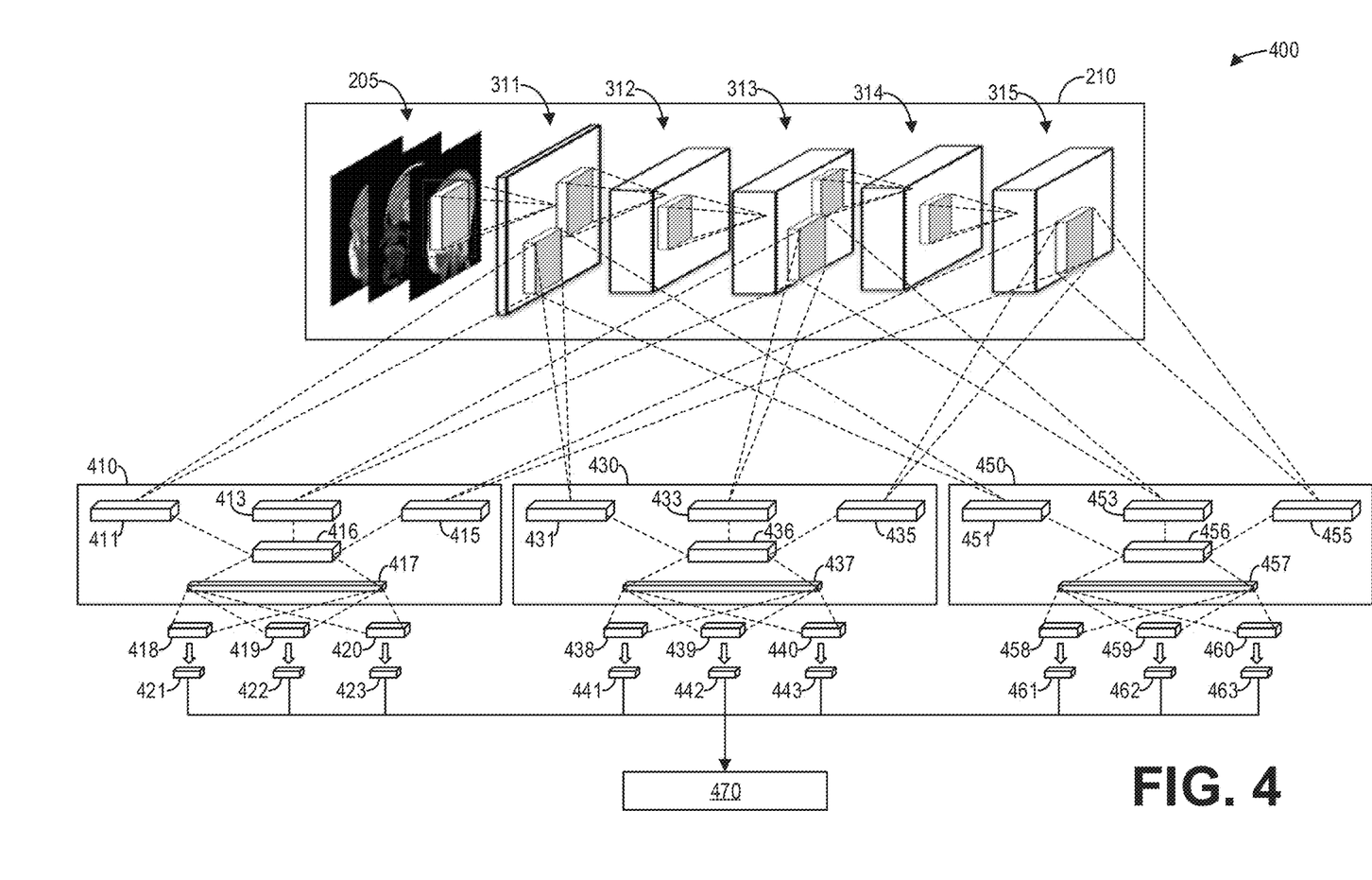
FIG. 4 shows a schematic diagram illustrating example layers of a deep learning architecture for generating a graphical prescription based on two-dimensional localizer images according to an exemplary embodiment.

FIG. 4 shows a schematic diagram illustrating example layers of a deep learning architecture 400 for generating a graphical prescription based on two-dimensional localizer images according to an exemplary embodiment. As discussed above, the two-dimensional localizer images may be two-dimensional localizers as acquired or reformatted (e.g., projected) from a three-dimensional localizer volume. The deep learning architecture 400 includes a plurality of hyper networks including a first hyper network 410 for generating graphical prescriptions for axial views, a second hyper network 430 for generating graphical prescriptions for sagittal views, and a third hyper network 450 for generating graphical prescriptions for coronal views. The combination of the hyper networks 410, 430, and 450 thus comprise the graphical prescription network 226. The combined output 470 therefore corresponds to the graphical prescription 236.

The outputs of at least a subset of the layers of the feature representation network 210 (e.g., the first convolutional layer 311, the third convolutional layer 313, and the fifth convolutional layer 315) are input respectively to a first convolutional layer 411, a second convolutional layer 413, and a third convolutional layer 415 of the first hyper network 410 for generating axial graphical prescriptions. The outputs of the first convolutional layer 411, the second convolutional layer 413, and the third convolutional layer 415 are then fused or input to a shared convolutional layer 416 of the first hyper network 410. The output of the shared convolutional layer 416 is input to a fully-connected layer 417. The output of the fully-connected layer 417 is input to a fully-connected layer 418 for axial dimension prescriptions, a fully-connected layer 419 for axial position prescriptions, and a fully-connected layer 420 for axial orientation prescriptions. The fully-connected layers 418, 419, and 420 thus respectively output axial dimension prescriptions 421, axial position prescriptions 422, and axial orientation prescriptions 423.

Similarly, the outputs of at least a subset of the layers of the feature representation network 210 are input respectively to a first convolutional layer 431, a second convolutional layer 433, and a third convolutional layer 435 of the second hyper network 430 for generating sagittal graphical prescriptions. The outputs of the first convolutional layer 431, the second convolutional layer 433, and the third convolutional layer 435 are then fused or input to a shared convolutional layer 436 of the second hyper network 430. The output of the shared convolutional layer 436 is input to a fully-connected layer 437. The output of the fully-connected layer 437 is then input to a fully-connected layer 438 for sagittal dimension prescriptions, a fully-connected layer 439 for sagittal position prescriptions, and a fully-connected layer 440 for sagittal orientation prescriptions. The fully-connected layers 438, 439, and 440 thus respectively output sagittal dimension prescriptions 441, sagittal position prescriptions 442, and sagittal orientation prescriptions 443.

The outputs of at least a subset of the layers of the feature representation network 210 are also input respectively to a first convolutional layer 451, a second convolutional layer 453, and a third convolutional layer 455 of the third hyper network 450 for generating coronal graphical prescriptions. The outputs of the first convolutional layer 451, the second convolutional layer 453, and the third convolutional layer 455 are then input to a shared convolutional layer 456 of the third hyper network 450. The output of the shared convolutional layer 457 is then input to a fully-connected layer 457 of the third hyper network 450. The output of the fully-connected layer 457 is then input to a fully-connected layer 458 for coronal dimension prescriptions, a fully-connected layer 459 for coronal position prescriptions, and a fully-connected layer 460 for coronal orientation prescriptions. The fully-connected layers 458, 459, and 460 of the third hyper network 450 thus respectively output coronal dimension prescriptions 461, coronal position prescriptions 462, and coronal orientation prescriptions 463.

Finally, as depicted, the output of the first hyper network 410, the second hyper network 430, and the third hyper network 450 may be combined to form a set of graphical prescriptions 470 for axial, sagittal, and coronal views. The graphical prescriptions 470 thus include the dimension prescriptions 421 for axial views, the dimension prescriptions 441 for sagittal views, and the dimension prescriptions 461 for coronal views. The graphical prescriptions 470 further include the position prescriptions 422 for axial views, the position prescriptions 442 for sagittal views, and the position prescriptions 462 for coronal views. The graphical prescriptions 470 further include the orientation prescriptions 423 for axial views, the orientation prescriptions 443 for sagittal views, and the orientation prescriptions 463 for coronal views.

It should be appreciated that in some examples, the hyper networks 410, 430, and 450 may not generate dimension, position, and orientation prescriptions. As an illustrative and non-limiting example, the hyper networks 410, 430, and 450 may only generate position prescriptions 422, 442, and 462.

In such an example, the hyper networks 410, 430, and 450 may not include, the fully-connected layers 418, 420, 438, 440, 458, and 460.

In some embodiments where three-dimensional localizer images are used without being transformed to two-dimensional, the graphical prescription neural network 350 may consist of one hyper neural network for generating graphical prescriptions of a three-dimensional volume using the three-dimensional localizer images.

Figure 5:
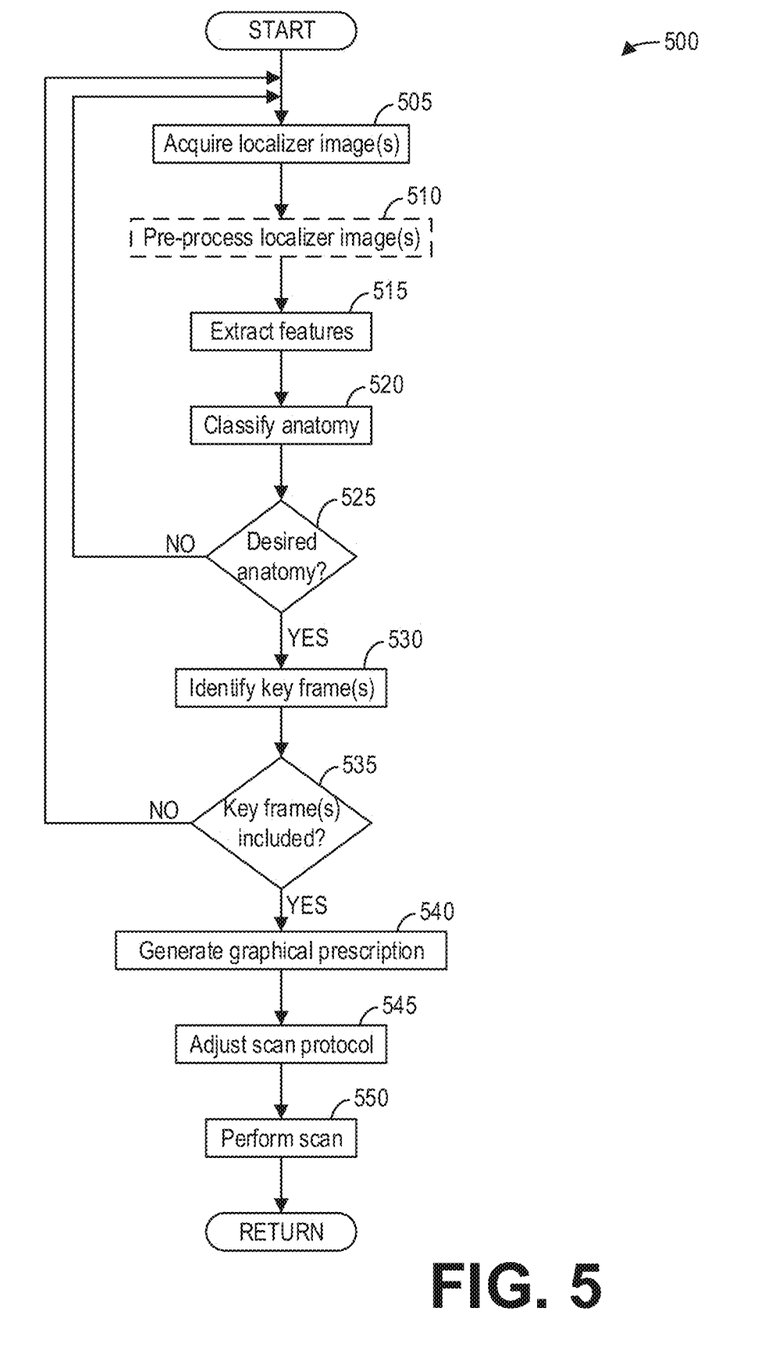
FIG. 5 shows a high-level flow chart illustrating a method for automatically generating a graphical prescription according to an exemplary embodiment.

FIG. 5 shows a high-level flow chart illustrating an example method 500 for automatically generating a graphical prescription according to an embodiment. In particular, method 500 relates to automatically generating a graphical prescription by applying localizer images to a deep neural network system, such as the deep neural network systems depicted in FIGS. 2-4. Method 500 is described with regard to the systems and components of FIGS. 1-4, though it should be appreciated that the method 500 may be implemented with other systems and components without departing from the scope of the present disclosure. Method 500 may be implemented in the MRI apparatus 10, or any appropriate combination of the MRI apparatus 10, an edge device connected to the MRI apparatus 10, a cloud in communication with the MRI apparatus 10, and so on.

Method 500 begins at 505. At 505, localizer images or scout images of a subject are acquired. The localizer images may be two-dimensional or three-dimensional. The localizer images may comprise standard SSFSE/GRE localizers, three-dimensional low-resolution volumes, or other two-dimensional localizers with T2/T1/PD contrasts depending on anatomy or clinical needs. A sagittal T2 FSE scan may be used to identify the multi-plane multi-angle axial scan.

At 510, the localizer images are pre-processed. Since the original localizer images may come from different systems with different shading patterns, and with different pulse sequences resulting in different contrasts, the localizer images may be pre-processed to normalize the localizer images. To that end, global contrast normalization may be performed to prevent images from having varying amounts of contrast by subtracting the mean from each image, and then rescaling the subtracted images so that the standard deviation across the pixels of the image is equal to a selected constant. In some cases, both global contrast normalization and local contrast normalization may be applied to ensure that edges and corners are effectively normalized. In some embodiments, the operation 510 may be omitted.

Further, in some examples, the localizer image data may be re-sampled and/or re-formatted in different orientations to provide additional inputs to the feature representation network. Furthermore, in embodiments wherein the localizer images are three-dimensional, the three-dimensional images may be projected into multi-plane two-dimensional space.

At 515, features are extracted from the localizer images by using a trained deep neural network (e.g., the feature representation network 210). In particular, the acquired or pre-processed localizer images are input into the feature representation network 210. The feature representation network convolves the localizer images across multiple convolutional layers to automatically extract features of the localizer images.

Continuing at 520, the anatomy of the localizer images is classified by using a trained neural network (e.g., the anatomy classification network 222). For example, the output of the final convolutional layer 315 of the feature representation network 210 is input to the anatomy classifier neural network 320, as shown in FIG. 3A. As another example, the outputs of multiple convolutional layers, such as convolutional layers 311, 313, and 315, of the feature representation network 210 are input to the hyper anatomy classification network formed by the hyper network 330 and the fully-connected layer 320', as shown in FIG. 3B.

Continuing at 525, it is determined whether the classified anatomy at 520 is a desired anatomy. For example, a specific anatomy (e.g., brain, shoulder, knee, etc.) is desired to be scanned for a subject. If the classified anatomy is not the desired anatomy (i.e., "NO" at 525), the localizer images either do not include the desired anatomy or the localizer images are not of sufficient image quality for positively classifying the anatomy in the images. Method 500 therefore returns so that localizer images may be acquired again at 505.

However, referring again to 525, if the classified anatomy is the desired anatomy (i.e., "YES" at 525), the desired anatomy is therefore present in the localizer images acquired at 505. Method 500 continues to 530. At 530, key frames are identified in the localizer images by using a trained neural network (e.g., the key frame identifier network 224). For example, the outputs from the convolutional layers 311, 313, and 315 of the feature representation network 210 are input to the hyper key frame identification network formed by the hyper network 330 and the fully-connected layer 350, as shown in FIGS. 3A and 3B. The hyper key frame identification network then outputs key frame(s) identified in the localizer images.

At 535, it is determined whether one or more key frames are included in the localizer images. If key frames are not included in the localizer images (i.e., "NO" at 535), method 500 returns so that additional localizer images may be acquired at 505. However, if one or more key frames are included in the localizer images (i.e., "YES" at 535), method 500 continues to 540. At 540, a graphical prescription is generated by using a trained neural network (e.g., the graphical prescription network 226). For example, the convolved results from the convolutional layers 311, 313, and 315 of the feature representation network 210 are input to one or more hyper networks for automatically generating graphical prescriptions. In some embodiments where two-dimensional localizer images are used, multiple hyper networks (e.g., hyper networks 410, 430, and 450) are used for multiple reference planes (e.g., axial, sagittal, and coronal). In some embodiments where three-dimensional localizer images are used without being transformed to two-dimensional, one hyper neural network is used for generating graphical prescriptions of a three-dimensional volume Continuing at 545, a scan protocol is adjusted according to the graphical prescription and the key frame(s). In some embodiments, an operator of the imaging system may first confirm, via the operator console unit 32, that the key frames and the graphical prescription displayed via display unit 33 accurately prescribe the coverage and orientation for the desired region of interest. In such examples, the operator may manually adjust the scan protocol according to the graphical prescription. In some embodiments, the scan protocol is automatically adjusted according to the graphical prescription, as operator intervention may be unnecessary if the accuracy of the neural network system is sufficient for ensuring that the desired region of interest will be correctly imaged with sufficient coverage. In either case, at 550, a scan is performed according to the adjusted scan protocol. Method 500 then returns.

Figure 6:
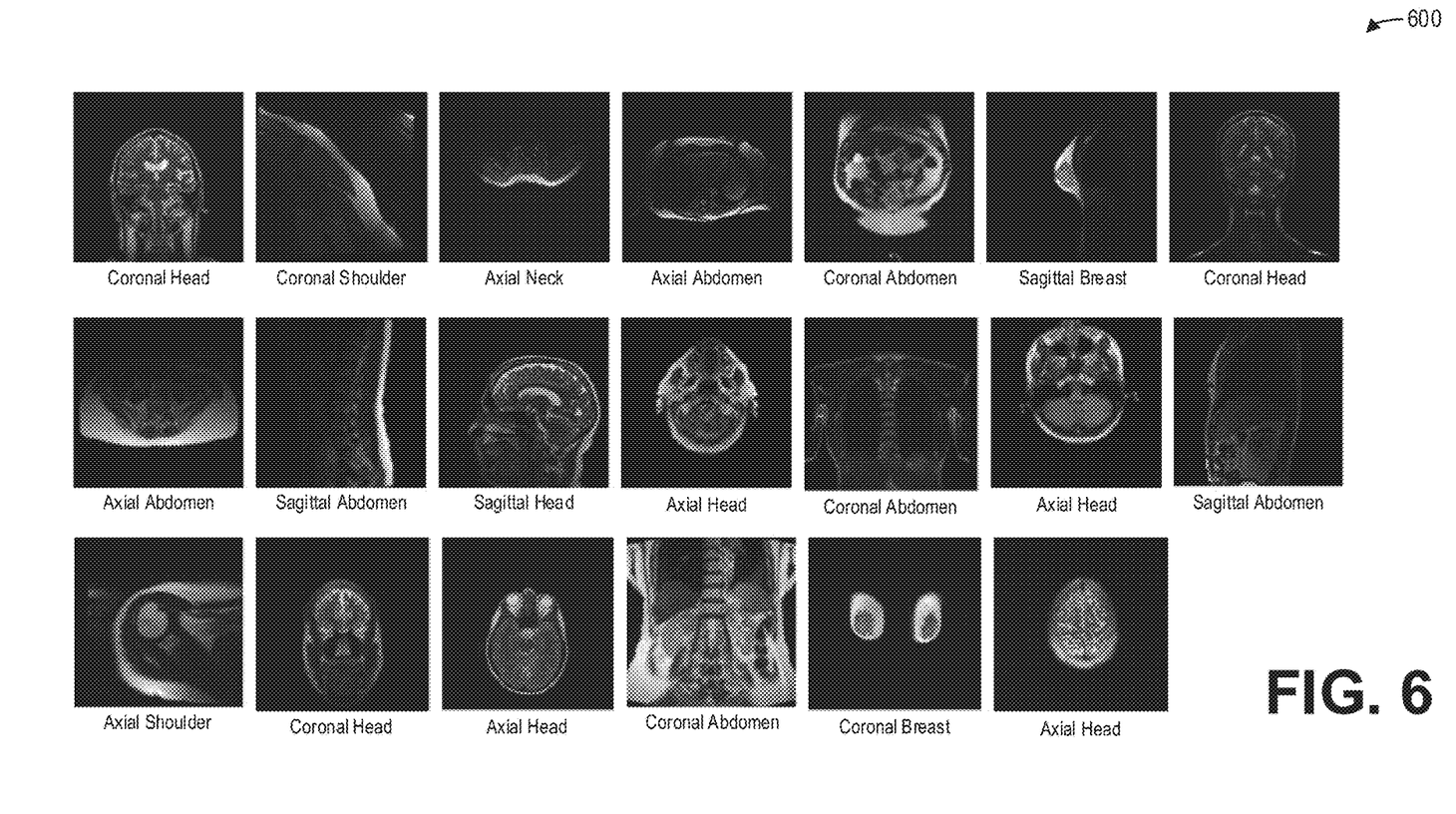
FIG. 6 shows a plurality of localizer images successfully classified according to anatomy according to an exemplary embodiment.

To illustrate the efficacy of the systems and methods described hereinabove, FIG. 6 shows a plurality of localizer images 600 successfully classified according to anatomy and reference plan by an anatomy classification neural network such as anatomy classification network 222 or anatomy classification network 320. After training the anatomy classification network with 24,380 localizer images, labeled according to seventeen categories (axial head, axial neck, axial chest, axial abdomen, axial breast, sagittal head, sagittal neck, sagittal breast, sagittal shoulder, sagittal abdomen, coronal head, coronal neck, coronal breast, coronal abdomen, coronal shoulder, and edge slice), the anatomy classification network successfully classified localizer images according to anatomy and reference plane with 98.8% accuracy when tested with 4,876 localizer images. The plurality of localizer images 600 comprise a sample of the successfully classified localizer images used during testing, and FIG. 6 depicts the corresponding anatomy and reference plane classifications generated by the trained anatomy classification network.

Figure 7:
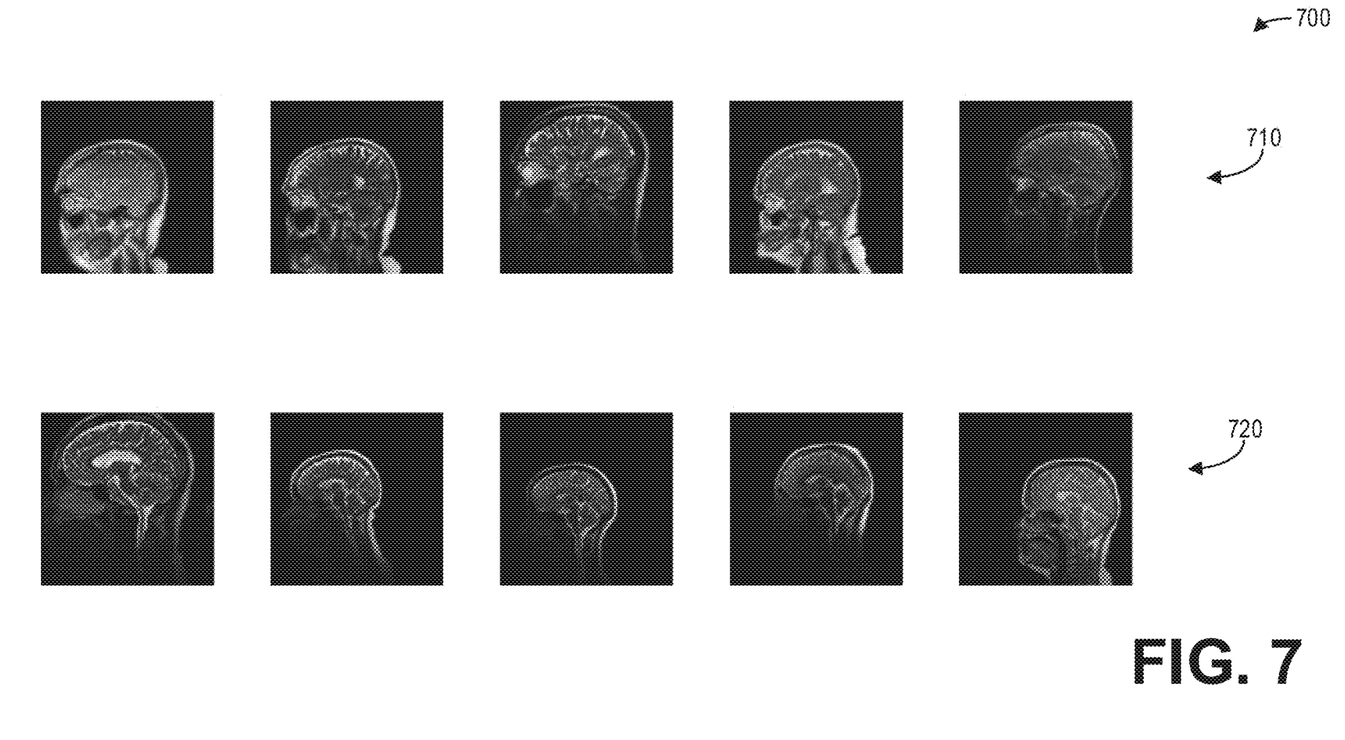
FIG. 7 shows a plurality of localizer images successfully classified as key frames or non-key frames according to an exemplary embodiment.

Furthermore, as discussed above, if the localizer images depict a brain of a subject, the key frames identified by the key frame identifier neural network may include the images of the localizer images that include the anterior commissure-posterior commissure (AC-PC) line, which comprises the line that connects two distinct anatomic structures of the brain, namely the anterior commissure (AC) and the posterior commissure (PC) of the brain. As an illustrative example, FIG. 7 depicts a plurality of localizer images 700 classified by a key frame identifier network such as the key frame identifier network 224 described hereinabove with regard to FIGS. 2, 3A, and 3B. The plurality of localizer images 700 includes localizer images 710 that the key frame identifier network classified as not including the AC-PC line, as well as localizer images 720 that the key frame identifier network classified as including the AC-PC line. As depicted, the key frame identifier network accurately distinguished between the localizer images 710 that do not include the AC-PC line from localizer images 720 that include the AC-PC line. In particular, the key frame identifier network successfully identified key frames including the AC-PC line with 97.1% accuracy after training the key frame identifier network with 3,000 sagittal head localizer images including 376 images labeled as key frames that include AC-PC line.

Figure 8:
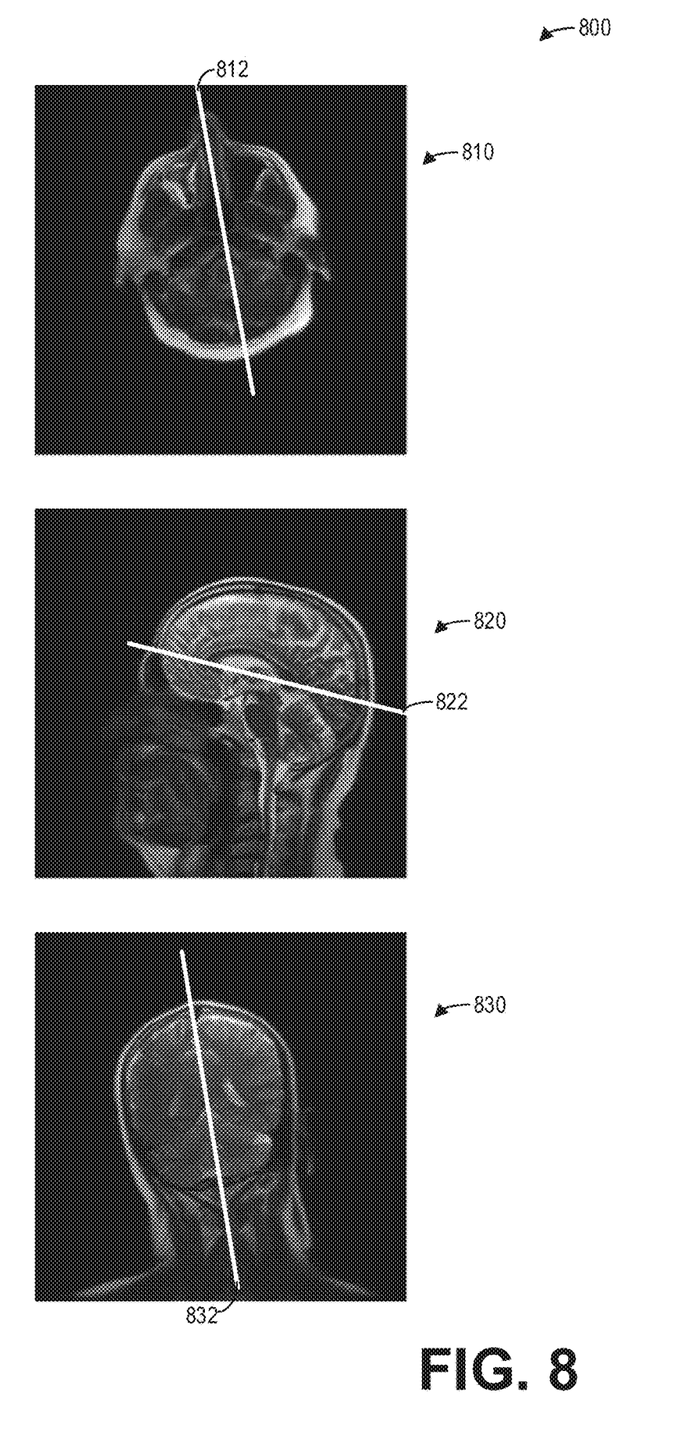
FIG. 8 shows a plurality of localizer images with automatically generated graphical prescriptions according to an exemplary embodiment.

FIG. 8 shows a plurality of localizer images 800 with graphical prescriptions automatically generated by a graphical prescription network such as the graphical prescription network 226 described hereinabove with regard to FIGS. 2 and 4. The graphical prescription network was trained with 1,000 images for each axis and tested on 200 images. The graphical prescription comprises key frames of the localizer images with the landmark visually or graphically identified in the key frame. For example, the localizer image 810 comprises an axial view of the head, with the AC-PC line 812 superimposed on the localizer image 810. Similarly, the localizer image 820 comprises a sagittal view of the head, with the AC-PC line 822 superimposed on the localizer image 820. The localizer image 830 comprises a coronal view of the head, with the AC-PC line 832 superimposed on the localizer image 830. The graphical prescription may further include orientation prescriptions for adjusting the scan, including but not limited to a translational shift in a first direction, a translational shift in a second direction, and a rotation relative to the reference planes depicted in the localizer images.

Thus, a deep learning framework for automated graphical prescription comprises three levels of neural networks which can be trained to learn the representation from the localizer images, including a hyper anatomy network to identify anatomy information, a hyper key frame network to identify key images or frames with critical anatomical structure information, and a hyper graphical prescription network comprising three networks for predicting in-plane graphical prescription information for axial, sagittal, and coronal localizer images. All of the neural networks adopt a fusion structure from the first layers and medium layers to the last layers to learn both low level and high level topological information.

A technical effect of the disclosure includes the automatic generation of a graphical prescription for imaging a desired region of interest. Another technical effect of the disclosure includes the automatic identification of key frames, anatomical landmarks, and reference planes within localizer images. Yet another technical effect of the disclosure includes the automatic scanning of a subject according to a graphical prescription generated by a deep neural network system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method for a medical imaging system, comprising:
acquiring, by the medical imaging system, localizer images of a subject;
extracting, by a trained feature representation neural network, features of the localizer images;
generating, by a trained graphical prescription neural network, a graphical prescription using output of the trained feature representation neural network;
generating, by a trained anatomy classification neural network, a classification of anatomy in the localizer images;
identifying, by a trained key frame identification neural network, key frames of the localizer images;
determining, by the trained key frame identifier network, a key frame from the localizer images of the subject, the anatomy classification neural network and the key frame identifier neural network receiving output in parallel from a feature representation network receiving the localizer images;
determining whether the classified anatomy is a desired anatomy;

responsive to determining that the classified anatomy is the desired anatomy, determining whether the key frame is included in the localizer images;

responsive to the classified anatomy not being the desired anatomy and in response to the key frame not being included, acquiring additional localizer images;

responsive to the classified anatomy being the desired anatomy and the key frame being included, generating, by a trained neural network system receiving the output in parallel from the feature representation network, a graphical prescription using the localizer images; and performing, by the medical imaging system, a scan of the subject according to the graphical prescription.

2. The method of claim 1, wherein the trained neural network system comprises the trained feature representation neural network and the trained graphical prescription neural network.

3. The method of claim 2, wherein the trained neural network system further comprises the trained anatomy classification neural network.

4. The method of claim 2, wherein the trained neural network system further comprises the trained key frame identification neural network.

5. The method of claim 2, wherein the trained feature representation neural network comprises a convolutional neural network.

6. The method of claim 2, wherein the trained graphical prescription neural network comprises separate hyper neural networks for generating graphical prescriptions of axial, sagittal, and coronal planes using two-dimensional localizer images.

7. The method of claim 2, wherein the trained graphical prescription neural network consists of one hyper neural network for generating graphical prescriptions of a three-dimensional volume using three-dimensional localizer images.

8. The method of claim 1, further comprising pre-processing the localizer images to normalize contrast across the localizer images.

9. The method of claim 1, wherein the localizer images comprise a three-dimensional localizer image volume, and the method further comprises projecting the three-dimensional localizer image volume into multi-plane two-dimensional localizer images.

10. The method of claim 1, wherein the graphical prescription indicates volume coverage and volume orientation of a desired region of interest of the subject, and wherein performing the scan of the subject according to the graphical prescription comprises scanning the desired region of interest of the subject according to the volume coverage and volume orientation indicated by the graphical prescription.

11. A method for an imaging system, comprising:

classifying, by a trained anatomy classification neural network, an anatomy from localizer images of a subject;

determining, by a trained key frame identifier network, a key frame from the localizer images of the subject, the anatomy classification network and the key frame identifier network receiving output in parallel from a feature representation network receiving the localizer images;

determining whether the classified anatomy is a desired anatomy;

in response to determining that the classified anatomy is the desired anatomy, determining whether the key frame is included in the localizer images;

in response to the classified anatomy not being the desired anatomy and in response to the key frame not being included, acquiring additional localizer images; and in response to the classified anatomy being the desired anatomy and the key frame being included, generating, by a trained graphical prescription neural network receiving the output in parallel from the feature representation network, a graphical prescription for imaging the subject.

12. The method of claim 11, wherein the trained anatomy neural network and the trained key frame identifier neural network share a plurality of convolutional layers.

13. The method of claim 11, wherein the localizer images are magnetic resonance (MR) localizers and the graphical prescription is for MR scan.

14. The method of claim 11, wherein the localizer images are two-dimensional, and the trained graphical prescription neural network comprises separate hyper neural networks for generating graphical prescriptions of axial, sagittal, and coronal planes using the two-dimensional localizer images.

15. The method of claim 11, wherein the localizer images are three-dimensional, and the trained graphical prescription neural network consists of one hyper neural network for generating graphical prescriptions of a three-dimensional volume using the three-dimensional localizer images.

16. A medical imaging system, comprising:

a medical scanning apparatus for scanning a subject;

a memory storing a trained neural network system; and a processor communicatively coupled to the medical scanning apparatus and the memory and configured to:

control the medical scanning apparatus to acquire localizer images of the subject;

cause the trained neural network system to classify an anatomy from the localizer images of a subject;

cause the trained neural network to determine a key frame from the localizer images of the subject, the trained neural network system receiving output in parallel from a feature representation network receiving the localizer images;

determine whether the classified anatomy is a desired anatomy;

responsive to a determination that the classified anatomy is the desired anatomy, determine whether the key frame is included in the localizer images;

responsive to the classified anatomy not being the desired anatomy and in response to the key frame not being included, acquire additional localizer images; and responsive to the classified anatomy being the desired anatomy and the key frame being included, generate, with the trained neural network system receiving the output in parallel from the feature representation network, a graphical prescription using the localizer images, the graphical prescription indicating a volume coverage and orientation for a desired region of interest of the subject.

17. The medical imaging system of claim 16, wherein the trained neural network system is configured to automatically classify anatomies and identify key frames within the localizer images.

18. The medical imaging system of claim 17, wherein the trained neural network system comprises a plurality of fully-connected layers for separately generating the graphical prescription, identifying the key frames, and identifying the anatomies, wherein each of the plurality of fully-connected layers receive inputs from a common plurality of convolutional layers that extract features from the localizer images.

19. The medical imaging system of claim 16, wherein the processor is further configured to adjust a scan protocol according to the graphical prescription.

20. The medical imaging system of claim 19, wherein the processor is further configured to control the medical scanning apparatus to scan the subject according to the adjusted scan protocol.

* * * * *